United States Patent [19]

Houlihan

[11] 3,931,176

[45] Jan. 6, 1976

[54] HYDROXYALKYL SUBSTITUTED-4,5-DIHYDROPYRIDAZIN(2H)-3-ONES

[75] Inventor: William J. Houlihan, Mountain Lakes, N.J.

[73] Assignee: Sandoz Inc., E. Hanover, N.J.

[22] Filed: Oct. 25, 1973

[21] Appl. No.: 409,653

Related U.S. Application Data

[63] Continuation-in-part of Ser. No. 366,670, June 4, 1973, abandoned, which is a continuation-in-part of Ser. No. 182,159, Sept. 20, 1971, abandoned, which is a continuation-in-part of Ser. No. 166,565, July 27, 1971, abandoned, which is a continuation-in-part of Ser. No. 88,976, Nov. 12, 1970, abandoned.

[52] U.S. Cl.... 260/250 A; 260/250 P; 260/250 AC; 424/250
[51] Int. Cl.² .................................. C07D 237/04
[58] Field of Search ..... 260/250 AH, 250 A, 250 P, 260/250 AC

[56] References Cited
UNITED STATES PATENTS

| | | | |
|---|---|---|---|
| 3,497,512 | 2/1970 | Hofer | 260/250 A |
| 3,549,620 | 12/1970 | Houlihan | 260/250 A |
| 3,657,242 | 4/1972 | Houlihan | 260/250 A |

FOREIGN PATENTS OR APPLICATIONS

| | | | |
|---|---|---|---|
| 1,544,700 | 9/1968 | France | 260/250 A |

*Primary Examiner*—Donald G. Daus
*Assistant Examiner*—Anne Marie T. Tighe
*Attorney, Agent, or Firm*—Gerald D. Sharkin; Robert S. Honor; Thomas O. McGovern

[57] ABSTRACT

Hydroxyalkyl and aryl or heterocyclic substituted-4,5-dihydropyridazin(2H)-3-ones and diazabicyclo-ene-ones e.g., 6-(p-chloro-phenyl)-2-(2-hydroxybutyl)-4,5-dihydropyridazin(2H)-3-one are prepared by condensing 1-hydrazino-2-alkanols with aryl or heterocyclic-γ-keto acids and are useful as central nervous system depressants.

12 Claims, No Drawings

HYDROXYALKYL SUBSTITUTED-4,5-DIHYDROPYRIDAZIN(2H)-3-ONES

This application is a continuation-in-part of copending U.S. patent application Ser. No. 366,670, filed June 4, 1973 now abandoned which in turn is a continuation-in-part of copending U.S. patent application Ser. No. 182,159, filed Sept. 20, 1971 now abandoned which in turn is a continuation-in-part of U.S. patent application, Ser. No. 166,565, filed July 27, 1971 now abandoned which in turn is a continuation-in-part of copending U.S. patent application, Ser. No. 88,976, filed Nov. 12, 1970 now abandoned.

This invention relates to derivatives of 4,5-dihydropyridazin(2H)-3-ones and diazabicyclo-ene-ones. More particularly, it relates to (2-hydroxyalkyl) and aryl or heterocyclic substituted-4,5-dihydropyridazin(2H)-3-ones and diazabicylo ene-ones, to methods for their preparation and to their use in pharmaceutical compositions.

The compounds of this invention may be represented by the following formula:

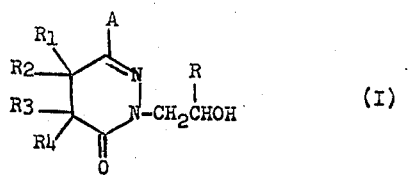

(I)

where
R is lower alkyl having 1 to 4 carbon atoms, i.e., methyl, ethyl, isopropyl, etc;
$R_1$, $R_2$, $R_3$, and $R_4$ each independently represent hydrogen or lower alkyl having 1 to 4 carbon atoms or
$R_1$ and $R_4$ represent hydrogen and
$R_2$ and $R_3$ together represent

where
n is 2, 3, or 4 and
A represents

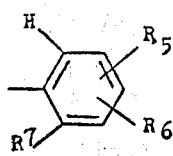 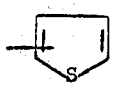 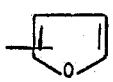

or

where
$R^7$ represents hydrogen; halo having an atomic weight of from about 19 to 36 or straight chain lower alkyl having 1 to 4 carbon atoms; and $R_5$ and $R_6$ each independently represent hydrogen, halo having an atomic weight of about 19 to 36, trifluoromethyl or lower alkyl having 1 to 4 carbon atoms provided that when both $R^5$ and $R^6$ represent trifluoromethyl, they are on other than adjacent carbon atoms and that at least one of $R^5$, $R^6$ and $R^7$ is hydrogen.

The compounds of formula (I) are prepared in accordance with the following process:

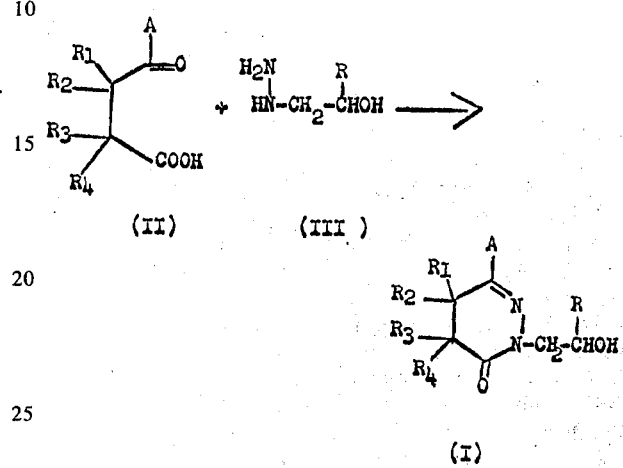

where R, $R_1$, $R_2$, $R_3$, $R_4$, A and the proviso are as set out above.

The compounds of formula (I) are prepared by condensing a γ-ketobutyric acid of formula (II) with a 1-hydrazino-2-alkanol of formula (III). The reaction is preferably run in inert solvents, e.g., aromatic and chloro substituted aromatic hydrocarbons, especially toluene, xylene, chlorobenzene and dichlorobenzene. The condensation may be carried out by heating a mixture of a compound of formula (II) and a compound of formula (III) in an inert solvent at temperatures of from about 60° to 200°C., preferably at the reflux temperatures of the system. Neither the particular solvent nor the temperature at which the reaction is carried out is critical.

The condensation can also be carried out in the presence of an acid catalyst, such as an arylsulfonic acid, e.g., para-toluene sulfonic acid monohydrate. Preferably, the water formed during the reaction is removed by selecting a solvent which forms an azeotrope with water but is water immiscible, thereby permitting use of a Dean-Stark tube to remove the water from the reaction system. While the compound of formula (II), theoretically, react with compounds of formula (III) in a molar ratio of 1:1 to form the corresponding compounds of formula (I), it is preferred that the condensation be carried out using a molar excess, e.g., 10 to 100% of the compound of formula (III). The final product is recovered by conventional techniques, e.g., evaporation and recrystallization.

The compounds of formula (I) can also be prepared in accordance with the following process:

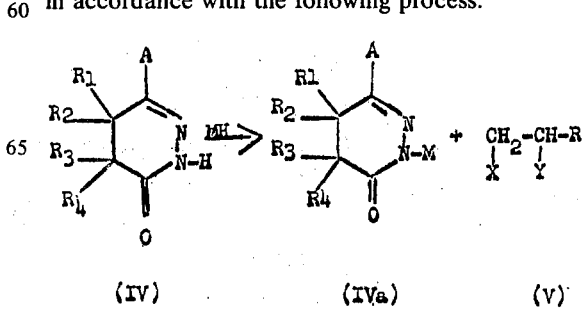

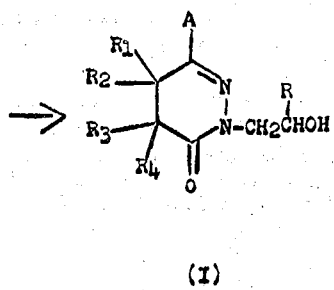

(I)

where
M is an alkali metal;
X is halo having an atomic weight of about 35 to 80;
Y is hydroxy or
X and Y together represent —O— and
R, $R_1$, $R_2$, $R_3$, $R_4$, A and the proviso are as set out above The compounds of formula (I) are prepared by treating a compound of formula (IV) with an alkali metal hydride and then treating the intermediate (IVa) with a compound of formula (V) in an inert solvent at a temperature not above 50°C preferably in an inert atmosphere. The inert atmosphere can be any of the usual inert gases, e.g., argon, helium or nitrogen, preferably nitrogen. The alkali metal hydride can be lithium, sodium or potassium hydride, preferably sodium hydride. Although the particular solvent used is not critical dimethylformamide (DMF), dimethylacetamide (DMA), aliphatic hydrocarbons such as hexane and heptane, and aromatic hydrocarbons such as benzene and toluene are preferred. DMF or DMA or mixtures of DMF or DMA with aromatic hydrocarbons are especially preferred. The particular temperature used is not critical, but it is preferred that the reaction be run at 10° to 50°C, especially 15° to 30°C. For optimum results, the reaction should be run for 6 to 24 hours, preferably 6 to 16 hours. The product is recovered using conventional techniques, e.g., evaporation. The compounds of formula (I) can also be prepared by the following process:

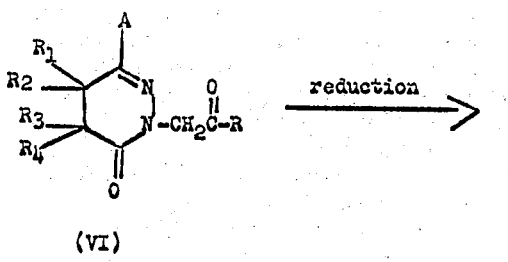

(VI)

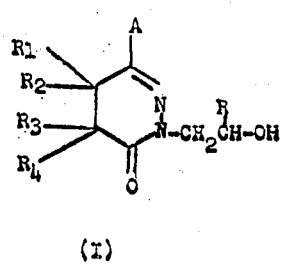

(I)

where $R, R_1, R_2, R_3, R_4$, A and the proviso are set out above.

The compounds of formula (I) are prepared by reducing a compound of formula (VI) with an alkali metal borohydride in an aqueous solvent. The alkali metal borohydride can be lithium, sodium or potassium borohydride, preferably sodium borohydride. The aqueous solvent can be water or water plus an inert water miscible organic solvent, preferably lower alkanols, such as methanol, ethanol or isopropanol. The temperature of the reaction is not critical; and the process can be carried at from 20°C to 100°C preferably 50° to 75°C. For optimum results the reaction should be run for about 2 to 6 hours. The product is recovered by conventional methods, e.g. evaporation.

The compounds of formula (VI) are prepared in accordance with the following flow diagram:

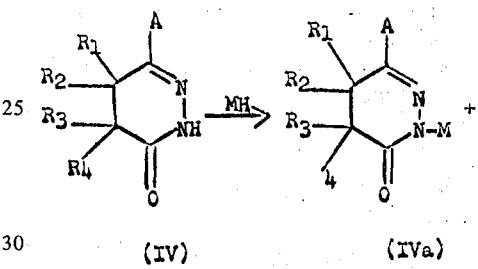

(IV)          (IVa)

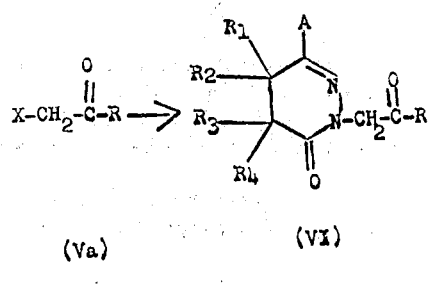

(Va)          (VI)

where R, $R_1$, $R_2$, $R_3$, $R_4$, A, M and X are as defined above.

The reaction conditions for preparing compound (VI) are the same as in the process above for preparing compound (I) from compounds (IVa) and (V).

Certain of the compounds of formulas (II) (III), (IV), (IVa), (V) and (Va) are known and can be prepared by methods described in the literature. The compounds of formulas (II), (III), (IV), (IVa), (V) and (Va) not specifically disclosed can be prepared from known starting materials by methods analogous to those described in the literature.

The compounds of formula (I) in which $R^2$ and $R^3$ represent

exist as geometrical isomers, (isomer A and isomer B). These isomers can be separated by conventional means e.g., fractional crystallization, and both forms are included in this invention. All of the compounds of formula (I) also occur as optical isomers, which can be separated by conventional means; and these isomer forms are also included in this invention.

The compounds of formula (I) are useful because they possess pharmacological activity in animals. In particular, the compounds are useful as central nervous system depressants, especially as minor tranquilizers, anti-convulsants, and muscle relaxants as indicated (1) by their ability to produce docility in behavior tests in mice given 25 to 200 milligrams per kilogram of animal body wieght, i.p. of the test compound according to the 30-word adjective check sheet system basically as described by Irwin, S. (Gordon Research Conference, Medicinal Chemistry 1959) and Chen (Symposium on Sedative and Hypnotic Drugs, Williams and Wilkins, 1954); (2) by the method of Orloff, et al. (Proc. Soc. Exp. Biol., 70:254, 1949) using mice given 25 to 200 milligrams per kilograms of animal body weight, i.p. of the test compound after convulsive seizures are chemically induced with strychnine and metrazol; (3) by the convulsive seizure antagonism procedure in which 25 to 200 milligrams per kilogram of animal body weight of the test compound is administered intraperitoneally to 20 mice followed 1 hour later by 50 milligrams per kilogram of animal body weight, i.p. of N-sulfamoylazepine, a compound which causes a convulsant sequence including tonic convulsions and death similar to those seen with pentylenetetrazol; (4) by the hexobarbital reinduction method of Winter (J. Pharmacol & Exp. Therap., 97:7, 1948) in which reinduction of of anesthesia after recovery from hexobarbital induced anesthesia is used to determine sedative hypnotic activity in mice given 70 milligrams per kilogrma of animal body weight, i.p. of hexobarbital followed immediately after the mice regain their righting reflexes by 25 to 200 milligrams per kilogram of animal body weight, i.p. of the test compound and (5) by their ability to depress spinal reflexes measured by flexor and patellar responses using force displacement transducers in male cats given 2.5 to 20 milligrams per kilogram of animal body weight, i.v. of the test compound.

When the compounds are employed for the above utilities, they may be combined with one or more pharmaceutically acceptable carriers or adjuvants, and may be administered orally in such forms as tablets, capsules, elixirs, suspensions and the like parenterally in the form of an injectable solution or suspension or in special forms such as suppositories and the like. Depending upon the compound employed and the mode of administration the exact dosage utilized may vary.

However, in general, satisfactory results are obtained when the compounds are administered as minor tranquilizers, anti-convulsants or muscle relaxants at a daily dosage of from about 1 milligram to 200 milligrams per kilogram of animal body weight. This daily dosage is preferably given in divided doses, e.g., 2 to 4 times a day, or in sustained release form. For most large mammals, the total daily dosage is from about 75 to 2000 milligrams; preferably 75 to 500 milligrams; and dosage forms suitable for internal administration comprise from about 19 milligrams to about 1000 milligrams preferably 19 to 250 milligrams of the compound in admixture with a solid or liquid pharmaceutical carrier or diluent.

The preferred compounds of formula (I) are those in which R is ethyl, Ar is a substituted phenyl, and each of $R_1$, $R_2$, $R_3$ and $R_4$ are hydrogen. The compounds of formula (I) in which R is ethyl, each of $R_1$, $R_2$, $R_3$ and $R_4$ are hydrogen, and A is p-chlorophenyl, or 3,4-dichlorophenyl are especially useful as muscle relaxants.

Tablets and capsules containing the ingredients indicated below may be prepared by conventional techniques and are useful as muscle relaxants and in treating tension and anxiety at a dose of one tablet or capsule 2 to 4 times a day.

| Ingredients | Weight (mg) | |
|---|---|---|
| | tablet | capsule |
| 6-(2,4-dichlorophenyl)-2-(2-hydroxybutyl)-4,5-dihydropyridazin-(2H)-3-one | 100 | 100 |
| tragacanth | 10 | — |
| lactose | 147.5 | 200 |
| corn starch | 25 | |
| talcum | 15 | |
| magnesium stearate | 2.5 | |
| Total | 300 mg. | 300 mg. |

Similarly, tablets and capsules containing 50 milligrams per tablet or capsule of 6-(p-chlorophenyl)-2-(2-hydroxybutyl)-4,5-dihydropyridazin (2H)-3-one in place of the 6-(3,4-dichlorophenyl)-2-(2-hydroxybutyl)-4,5-dihydropyridazin(2H)-3-one can be prepared in the same manner as above and are useful as muscle relaxants and in treating anxiety and tension at a dose of one tablet or capsule 2 to 4 times a day.

The following pharmaceutical compositions are formulated with the indicated amount of active agent using conventional techniques. The injectable suspension and the oral liquid suspension represent formulations useful as unit doses and may be administered as muscle relaxant or in the treatment of tension or anxiety. The injectable suspension is suitable for administration twice a day whereas the oral liquid suspension is suitable administered 2 to 4 times per day for this purpose.

| Ingredient | Weight (mg) | |
|---|---|---|
| | Injectable | Oral Suspension |
| 6-(3,4-dichlorophenyl)-2-(2-hydroxybutyl 4,5-dihydropyridazin-(2H)-3-one | 50 | 50 |
| sodium carboxy methyl cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, USP | — | 4.5 |
| propyl paraben, U.S.P | — | 1.0 |
| polysorbate 80 (e.g. Tween 80), U.S.P. | — | 5 |
| sorbitol solution, 70%, USP | — | 2,500 |

| Ingredient | Weight (mg) | |
|---|---|---|
| | Injectable | Oral Suspension |
| buffer agent to adjust pH for desired stability | — | q.s. |
| water | for injection q.s. to 1 ml. | q.s. to 5 ml. |

Similarly, injectable and oral solution unit doses containing an equivalent amount of 6-(p-chlorophenyl)-2-(2-hydroxybutyl)-4,5-dihydropyridazin- (2H)-3-one in place of the 6-(3,4-dichlorophenyl)-2-(2-hydroxybutyl)-4,5-dihydropyridazin- (2H)-3-one can be prepared in the same manner as above and are useful as muscle relaxants and in treating anxiety and tension when administered 2 to 4 times a day for these purposes.

EXAMPLE 1

6-(p-Chlorophenyl)-2-(2-Hydroxybutyl)-4,5-Dihydropyridazin(2H)-3-One

To a flask equipped with a condenser, Dean-Stark tube and stirrer is added 10.6 g (0.05 mole) of 3-(p-chlorobenzoyl)-propionic acid, 6.2 g (0.06 mole) of 1 hydrazino-2-butanol and 250 ml of toluene. The mixture is stirred and refluxed until water ceases to separate in the Dean-Stark tube. The solvent is then removed in vacuo on a rotary evaporator and the residue is crystallized from ether to obtain 6-(p-chlorophenyl)-2-(2-hydroxybutyl)-4,5-dihydropyridazin(2H)-3-one, mp 95.5° – 97°C.

The 6-(p-chlorophenyl)-2-(2-hydroxybutyl)-4,5-dihydropyridazin(2H)-3-one of this example is useful as a muscle relaxant when administered at a dose of 50 milligrams 2 to 4 times a day.

Following the above procedure, but using an equivalent amount of 3-(p-fluorobenzoyl)-propionic acid; 3-(3,4-dichlorobenzoyl)-propionic acid; 3-(p-trifluoromethylbenzoyl)-propionic acid; 3-(3-methyl-4-chlorobenzoyl)-propionic acid or 3-(2,4-dichlorobenzoyl)-propionic acid in place of the 3-(p-chlorobenzoyl)-propionic acid, there is obtained 6-(p-fluorophenyl)-2-(2-hydroxybutyl)-4,5-dihydropyridazin(2H)-3-one (m.p. 85° – 87°C.), 6(3,4-dichlorophenyl)-2-(2-hydroxybutyl)-4,5-dihydropyridazin(2H)-3-one (m.p. 106.5°–108°C), 6-(p-trifluoromethylphenyl)-2-(2-hydroxybutyl-4,5-dihydropyridazin(2H)-3-one, 6-(3-methyl-4-chlorophenyl)-2-(2-hydroxybutyl)-4,5-dihydropyridazin(2H)-3-one(m.p. 92.5°–94°C) or 6-(2,4-dichlorophenyl)-2-(2-hydroxybutyl)-4,5-dihydropyridazin(2H)-3-one, respectively.

When the above procedure is carried out using equivalent amounts of 3-(p-fluorobenzoyl)-propionic acid and 1-hydrazino-2-hexanol,3-(3,4 dichlorobenzoyl)-propionic acid and 1-hydrazino -2-propanol or 3-(3,4-dichlorobenzoyl)-propionic acid and 1-hydrazino-2-hexanol in place of the 3-(p-chlorobenzoyl)-propionic acid and 1-hydrazino-2-butanol used therein, there is obtained 3-(p-fluorophenyl)-2-(2-hydroxyhexyl-4,5-dihydropyridazin (2H)-3-one(m.p. 75°–77°C) 3-(3,4-dichlorophenyl)-2-(2-hydroxypropyl)-4,5-dihydropyridazin (2H)-3-one (m.p. 108.5° – 100°C) or 3-(3,4-dichlorophenyl)-2-(2-hydroxyhexyl)-4,5-dihydropyridazin (2H)-3-one(m.p. 80°–81°C) respectively.

EXAMPLE 2

2-(2-Hydroxybutyl)-6-(2-Thienyl)-4,5-Dihydropyridazin(2H)-3-One

Following the procedure of Example 1. but using an equivalent amount of 3-(2-thenoyl)-propionic acid in place of the 3-(p-chlorobenzoyl)-propionic acid used therein, there is obtained 6-(2-thienyl)-2-(hydroxybutyl)-4,5-dihydropyridazin(2H)-3-one; mp 75° – 78°C.

When 3-picolinoyl propionic acid is used in place of 3-(2-thenoyl)-propionic acid in the above process, 6-(2-pyridyl)-2-(2-hydroxybutyl)-4,5-dihydropyridazin(2H)-3-one is obtained.

When the procedure of Example I is carried out using equivalent weights of 3-(2-thenoyl)-propionic acid in place of the 3-(p-chlorobenzoyl)-propionic acid used therein and 1-hydrazino-2-propanol or 1-hydrazino-2-hexanol in place of the 1-hydrazino-2-butanol, there is obtained 6-(2-thienyl)-2-(2-hydroxypropyl)-4,5-dihydropyridazin (2H)-3-one (m.p. 74° – 77°C), or 6-(2-thienyl)-2-(2-hydroxyhexyl)-4,5-dihydropyridazin(2H)-3-one(m.p. 92° – 93.5°C) respectively.

EXAMPLE 3

2-(p-Chlorophenyl)-4-(2-Hydroxybutyl)-3,4-Diazabicyclo-[4.2.0]oct-2-ene-5-One

Into a flask equipped with a stirrer, heating mantle and Dean-Stark water separator is charged 7.2 g (0.30 mole) of a mixture of cis-and trans-2-p-chlorobenzoylcyclobutane carboxylic acid, 3.5g(0.033 mole) of 1-hydrazino-2-butanol and 100 ml. of toluene. The mixture is stirred and refluxed until the water layer in the Dean-Stark tube remains constant (ca. 5 hr). The solvent is removed in vacuo on a rotary evaporator, and the residue is dissolved in hot diethyl ether and allowed to cool to room temperature. The resultant solid is filtered off and yields 2-(p-chlorophenyl)-4-(2-hydroxybutyl) 3,4-diazabicyclo [4.2.0]-oct-2-ene-5-one (Isomer B;m.p. 133°–135°). The filtrate is further concentrated to give Isomer A (m.p. 115.5° – 119°C).

Following the above procedure using equivalent weight of cis-, trans-2-p-chlorobenzoylcyclohexane carboxylic acid in place of the cis-, trans-2-p-chlorobenzoylcyclobutane carboxylic acid, there is obtained 4-(p-chlorophenyl)-2-(2-hydroxybutyl)4a, 5, 6, 7, 8, 8a-hexahydrophthalazin(2H)-1-one (isomer A; m.p. 130.5°–134°C and Isomer B; m.p. 102.5°–105.5°C).

When essentially the same process described above is carried out using an equivalent amount of 3-p-chlorobenzoyl butanoic acid; 3-p-chlorobenzoyl-2,2-dimethyl propionic acid or 3-p-chlorobenzoyl-2-methyl propionic acid in place of the cis-,trans-2-p-chlorobenzoylcyclobutanecarboxylic acid, there is obtained 6-(p-chlorophenyl)-2-(2-hydroxybutyl)-5-methyl-4,5-dihydropyridazin (2H)-3-one (m.p. 90.5°–91.5°C);6-(p- chlorophenyl)-4,4-dimethyl-2-(2-hydroxybutyl)-4,5-dihydropyridazin (2H)-3-one (m.p. 75°–76°C) or 6-(p-chlorophenyl)-2-(2-hydroxybutyl)-4-methyl-4,5-dihydropyridazin(2H)-3-one (m.p. 77°–79°C)

EXAMPLE 4

6-(p-Chlorophenyl)-2-(2-Hydroxybutyl)-4,5-Dihydropyridazin(2H)-3-One

Into a flask equipped with stirrer, condenser and thermometer are charged 10.5 g (0.05 mole) of 6-p-chlorophenyl-4,5-dihydro pyridazin (2H)-3-one and 150 ml dry dimethylformamide under a blanket of nitrogen gas. To this mixture is added, in one portion, 1.3 g (0.055 mole) of sodium hydride as a 50% mineral oil suspension (2.6g). The mixture is stirred for about 4 hours at room temperature and then 9.2 g (0.060 mole) of 1-bromo-2-butanol in 50ml dry DMF is added dropwise. The reaction mixture is maintained at an internal temperature of 20° ± 5°C and allowed to stand for 15 hours. The solvent is removed in vacuo and the residue is treated with 100 ml water and 100 ml of methylene chloride. The organic layer is separated and dried with magnesium sulphate. After filtration and removal of the solvent, there is obtained 6-(p-chlorophenyl) -2-(2-hydroxybutyl)-4,5-dihydropyridazin(2H)-3-one, m.p. 95.5°–97°C.

Following the above procedure but using an equivalent amount of 2-ethyloxirane in place of the 1-bromo-2-butanol, the same product is obtained.

When the process of this example is carried out using either 1-bromo-2-butanol or 2-ethyloxirane and an equivalent amount of the following:

a. 6-(2,4-dichlorophenyl)-4,5-dihydropyridazin(2H)-3-one
b. 6-(p-fluorophenyl)-4,5-dihydropyridazin(2H)-3-one
c. 6-(3,4-dichlorophenyl)-4,5-dihydropyridazin(2H)-3-one
d. 6-(p-trifluoromethylphenyl)-4,5-dihydropyridazin (2H)-3-one
e. 6-(3-methyl-4-chlorophenyl)-4,5-dihydropyridazin(2H)-3-one
f. 6-(2-methyl-4-chlorophenyl)-4,5-dihydropyridazin(2H)-3-one
g. 6-(2,4-dichlorophenyl)-4,5-dihydropyridazin(2H)-3-one
h. 6-(2-thienyl-4,5-dihydropyridazin(2H)-3-one
i. 6-(2-pyridyl)-4,5-dihydropyridazin(2H)-3-one
j. 6-(p-chlorophenyl)-5-methyl-4,5-dihydropyridazin(2H)-3-one
k. 6-(p-chlorophenyl)-4,4-dimethyl-4,5-dihydropyridazin(2H)-3-one
l. 6-(p-chlorophenyl)-4-methyl-4,5-dihydropyridazin(2H)-3-one
m. cis-, trans-2-(p-chlorophenyl)-3,4-diazabicyclo[4.2.0]-oct-2-ene-5-one or
n. cis-,trans-4-(p-chlorophenyl)-4a,5,6,7,8,8a-hexahydrophthalazin (2H)-1-one in place of the 6-p-chlorophenyl-4,5-dihydropyridazin(2H)-3-one used therein, there is obtained a. 6-(2,4-dichlorophenyl)-2-(2-hydroxybutyl)-4,5-dihydropyridazin(2H)-3-one
b. 6-(p-fluorophenyl)-2-(2-hydroxybutyl)-4,5-dihydropyridazin (2H)-3-one
c. 6-(3,4-dichlorophenyl)-2-(2-hydroxybutyl)-4,5-dihydropyridazin (2H)-3-one
d. 6-(p-trifluoromethylphenyl)-2-(2-hydroxybutyl)-4,5-dihydropyridazine (2H)-3-one
e. 6-(3-methyl-4-chlorophenyl)-2-(2-hydroxybutyl)-4,5-dihydropyridazine (2H)-3-one
f. 6-(2-methyl-4-chlorophenyl)-2-(2-hydroxybutyl)-4,5-dihydropyridazin(2H)-3-one
g. 6-(2,4-dichlorophenyl)-2-(2-hydroxybutyl)-4,5-dihydropyridazin (2H)-3-one
h. 6-(2-thienyl)-2-(2-hydroxybutyl)-4,5-dihydropyridazin(2H)-3-one, m.p. 75°–78°C
i. 6-(2-pyridyl)-2-(2-hydroxybutyl)-4,5-dihydropyridazin(2H)-3-one
j. 6-(p-chlorophenyl)-2-(2-hydroxybutyl)-5-methyl-4,5-dihydopyridazin (2H)-3-one
k. 6-(p-chlorophenyl)-2-(2-hydroxybutyl)-4,4-dimethyl-4,5-dihydropyridazin (2H)-3-one
l. 6-(p-chlorophenyl)-2-(2-hydroxybutyl)-4-methyl-4,5-dihydropyridazin (2H)-3-one
m. cis-,trans-2-(p-chlorophenyl)-4-(2-hydroxybutyl)-3,4-diazabicyclo [4.2.0]-oct-2-ene-5-one or
n. cis-,trans-4(p-chlorophenyl)-2-(2-hydroxybutyl)-4a,5,6,7,8,8a-hexahydrophthalazin-(2H)-1-one respectively.

When the above process is carried out using equivalent weights of 6-(p-fluorophenyl)-4,5-dihydropyridazin (2H)-3-one and 1-bromo-2-hexanol, 6-(3,4-dichlorophenyl)-4,5-dihydropyridazin (2H)-3-one and 1-bromo-2-propanol, 6-(3,4-dichlorophenyl)-4,5-dihydropyridazin (2H)-3-one and 1-bromo-2-hexanol, 6-(2-thienyl)-4,5-dihydropyridazin(2H)-3-one and 1-bromo-2-propanol or 6-(2-thienyl)-4,5-dihydropyridazin (2H)-3-one and 1-bromo-2-hexanol in place of the 6-p-chlorophenyl-4,5-dihydropyridazin(2H)-3-one and 1-bromo-2-butanol used therein, there is obtained 6-(p-fluorophenyl)-2-(2-hydroxyhexyl)-4,5-dihydropyridazin(2H)-3-one, 6-(3,4-dichlorophenyl)-2-(2-hydroxypropyl)-4,5-dihydropyridazin (2H)-3-one, 6-(3,4-dichlorophenyl)-2-(2-hydroxyhexyl)-4,5-dihydropyridazin(2H)-3-one, 6-(2-thienyl)-2-(2-hydroxypropyl)-4,5-dihydropyridazin(2H)-3-one or 6-(2-thienyl)-2-(2-hydroxyhexyl)-4,5-dihydropyridazin(2H)-3-one respectively.

EXAMPLE 5

6-(3,4-Dichlorophenyl)-2-(2-Hydroxybutyl)-4,5-Dihydropyridazine(2H)-3-One a. 6-(3,4-Dichlorophenyl)-2-(2-Oxobutyl)-4,5-Dihydropyridazin(2H)-3-One In manner analogous to Example 4, but employing, in place of the 6-(p-chlorophenyl)-4,5-dihydropyridazin (2H)-3-one, an approximately equivalent amount of 6-(3,4-dichlorophenyl)-4,5-dihydropyridazin (2H)-3-one, and in place of the 1-bromo-2-butanol, an approximately equivalent amount of 1-bromo-2-butanone, the title compound is obtained, m.p. 164°–165°C.

b. 6-(3,4-Dichlorophenyl)-2-(2-Hydroxybutyl)-4,5-Dihydropyridazin(2H)-3-One

To a flask, equipped with a stirrer and condenser, is charged 3.53 g (0.01 mole) of 6-(3,4-dichlorophenyl)-2-(2-oxobutyl)-4,5-dihydropyridazin (2H)-3-one, and 50 ml of methanol. The mixture is stirred and 0.4 g of sodium borohydride is added, portion wise, over a period of 5 minutes. The mixture is refluxed for 4 hours and cooled to room temperature. Acetic acid is carefully added until the pH (litmus) is 7. The organic phase is concentrated in vacuo to yield the title compound.

When the above process is carried out using an equivalent amount of:
a. 6-p-fluorophenyl-4,5-dihydropyridazin (2H)-3-one
b. 6-(p-chlorophenyl)-4,5-dihydropyridazin(2H)-3-one
c. 6-(p-trifluoromethylphenyl)-4,5-dihydropyridazin(2H)-3-one
d. 6-(3-methyl-4-chlorophenyl)-4,5-dihydropyridazin(2H)-3-one
e. 6-(2,4-dichlorophenyl)-4,5-dihydropyridazin(2H)-3-one
f. 6-(2-thienyl)-4,5-dihydropyridazin(2H)-3-one
g. 6-(2-pyridyl)-4,5-dihydropyridazin(2H)-3-one
h. 6-(p-chlorophenyl)-5-methyl-4,5-dihydropyridazin(2H)-3-one
i. 6-(p-chlorophenyl)-4,4-dimethyl-4,5-dihydropyridazin (2H)-3-one
j. 6-(p-chlorophenyl)-4-methyl-4,5-dihydropyridazin (2H)-3-one
k. cis-, trans-2-(p-chlorophenyl)-3,4-diazabicyclo[4.2.0] oct-2-ene-5-one or
l. cis-, trans-4-(p-chlorophenyl)-4a, 5,6,7,8,8a-hexahydrophthalazin(2H)-1-one in place of the 6-(3,4-dichlorophenyl)-4,5-dihydropyridazin(2H)-3-one used therein, there is obtained before reduction in step (b),
a. 6-(p-fluorophenyl)-2-(2-oxybutyl)-4,5-dihydropyridazine-(2H)-3-one
b. 6-(p-chlorophenyl)-2-(2-oxybutyl)-4,5-dihydropyridazin(2H)-3-one
c. 6-(p-trifluoromethylphenyl)-2-(2-oxybutyl)-4,5-dihydropyridazin (2H)-3-one
d. 6-(3-methyl-4-chlorophenyl)-2-(2-oxybutyl)-4,5-dihydropyridazine(2H)-3-one
e. 6-(2,4-dichlorophenyl)-2-(2-oxybutyl)-4,5-dihydropyridazine-(2H)-3-one
f. 6-(2-thienyl)-2-(2-oxybutyl)-4,5-dihydropyridazin (2H)-3-one, m.p. 75°-78°C
g. 6-(2-pyridyl)-2-(2-oxybutyl)-4,5-dihydropyridazin-(2H)-3-one
h. 6-(p-chlorophenyl)-2-(2-oxybutyl)-5-methyl-4,5-dihydropyridazin (2H)-3-one
i. 6-(p-chlorophenyl)-2-(2-oxybutyl)-4,4-dimethyl-4,5-dihydropyridazin (2H)-3-one
j. 6-(p-chlorophenyl)-2-(2-oxybutyl)-4-methyl-4,5-dihydropyridazin (2H)-3-one
k. cis-,trans-2-(p-chlorophenyl)-4-(2-oxybutyl)-3,4-diazabicyclo [4.2.0] oct-2-ene-5-one or
l. cis-,trans-4-(p-chlorophenyl)-2-(2-oxybutyl)-4a,5,6,7,8,8a-hexahydrophthalazin (2H)-1-one respectively;

and after reduction thereis obtained
a. 6-(p-fluorophenyl)-2-(2-hydroxybutyl)-4,5-dihydropyridazin (2H)-3-one
b. 6-p-chlorophenyl)-2-(2-hydroxybutyl)-4,5-dihydropyridazin(2H)-3-one
c. 6-(p-trifluoromethylphenyl)-2-(2-hydroxybutyl)-4,5-dihydropyridazin (2H)-3-one
d. 6-(3-methyl-4-chlorophenyl)-2-(2-hydroxybutyl)-4,5-dihydropyridazin(2H)-3-one
e. 6-(2,4-dichlorophenyl)-2-(2-hydroxybutyl)-4,5-dihydropyridazin (2H)-3-one
f. 6-(2-thienyl)-2-(2-hydroxybutyl)-4,5-dihydropyridazin(2H)-3-one one g. 6-(2-pyridyl)-2-(2-hydroxybutyl)-4,5-dihydropyridazine(2H)-3-one
h. 6-(p-chlorophenyl)-2-(2-hydroxybutyl)-5-methyl-4,5-dihydropyridazin(2H)-3-one
i. 6-(p-chlorophenyl)-2-(2-hydroxybutyl)-4,4-dimethyl-4,5-dihydropyridazin(2H)-3-one
j. 6-(p-chlorophenyl)-2-(2-hydroxybutyl)-4-methyl-4,5-dihydropyridazin(2H)-3-one
k. cis-, trans-2-(p-chlorophenyl)-4-(2-hydroxybutyl)-3,4-diazabicyclo [4.2.0] oct-2-ene-5-one or
l. cis-,trans-4(p-chlorophenyl)-2-(2-hydroxybutyl)-4a,5,6,7,8,8a-hexahydrophthalazin-(2H)-1-one respectively When the above process is carried out using equivalent weights of the following
a. 6-(p-fluorophenyl)-4,5-dihydropyridazin(2H)-3-one and 1-bromo-2-hexanone
b. 6-(3,4-dichlorophenyl)-4,5-dihydropyridazin(2H)-3-one and 1-bromo-2-propanone
c. 6-(3,4-dichlorophenyl)-4,5-dihydropyridazin(2H)-3-one and 1 bromo-2-hexanone
d. 6-(2-thienyl)-4,5-dihydropyridazin(2H)-1-one and 1-bromo-2-propanone or
e. 6-(2-thienyl)-4,5-dihydropyridazin(2H)-3-one and 1-bromo-2-hexanone in place of the 6-(3,4-dichlorophenyl)-4,5-dihydropyridazin(2H)-3-one and 1-bromo-2-butanone used therein, there is obtained before reduction in step (b),
a. 6-(p-fluorophenyl)-2-(2-oxyhexyl)-4,5-dihydropyridazin(2H)-3-one
b. 6-(-3,4-dichlorophenyl)-2-(2-oxypropyl)-4,5-dihydropyridazin(2H)-3-one
c. 6-(3,4-dichlorophenyl)-2-(2-oxyhexyl)-4,5-dihydropyridazin(2H)-3-one
d. 6-(2-thienyl)-2-(2-oxypropyl)-4,5-dihydropyridazin(2H)-3-one
e. 6-(2-thienyl)-2-(2-oxyhexyl)-4,5-dihydropyridazin(2H)-3-one respectively; and after reduction, there is obtained the following;
a. 6-(p-fluorophenyl)-2-(2-hydroxyhexyl)-4,5-dihydropyridazin(2H)-3-one
b. 6-(3,4-dichlorophenyl)-2-(3-hydroxypropyl)-4,5-dihydropyridazin (2H-3-one
c. 6-(3,4-dichlorophenyl)-2-(2-hydroxyhexyl)-4,5-dihydropyridazin(2H)-3-one
d. 6-(2-thienyl)-2-(2-hydroxypropyl)-4,5-dihydropyridazin(2H)-3-one or
e. 6-(2-thienyl)-2-(2-hydroxyhexyl)-4,5-dihydropyridazin(2H)-3-one respectively.

What is claimed is:
1. A compound of the formula:

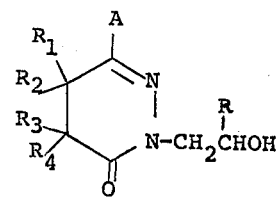

where
R is lower alkyl having 1 to 4 carbon atoms,
$R_1$, $R_2$, $R_3$, and $R_4$ each independently represent hydrogen or lower alkyl having 1 to 4 carbon atoms, and A represents

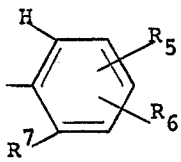

where
R[7] represents hydrogen; fluoro, chloro or straight chain lower alkyl having 1 to 4 carbon atoms, and R[5] and R[6] each independently represent hydrogen, fluoro, chloro, trifluoromethyl or lower alkyl having 1 to 4 carbon atoms provided that when both R[5] and R[6] represent trifluoromethyl, they are on other than adjacent carbon atoms and that at least one of R[5], R[6], and R[7] is hydrogen.

2. The compounds according to claim 1 in which $R_1$, $R_2$, $R_3$, and $R_4$ are hydrogen and R is ethyl.

3. The compound of claim 1 which is 6-(p-chlorophenyl)-2-(2-hydroxybutyl)-4,5-dihydropyridazin(2H)-3-one.

4. The compound of claim 1 which is 6-(3,4-dichlorophenyl)-2-(2-hydroxybutyl)-4,5-dihydropyridazin(2H)-3-one.

5. The compound of claim 1 which is 6-(p-fluorophenyl)-2-(2-hydroxybutyl)-4,5-dihydropyridazin(2H)-one.

6. The compound of claim 1 which is 6-(p-fluorophenyl)-2-(2-hydroxyhexyl)-4,5-dihydropyridazin(2H)-3-one.

7. The compound of claim 1 which is 6-(3,4-dichlorophenyl)-2-(2-hydroxypropyl)-4,5-dihydropyridazin(2H)-3-one.

8. The compound of claim 1 which is 6-(3,4-dichlorophenyl)-2-(2-hydroxyhexyl)-4,5-dihydropyridazin(2H)-3-one.

9. The compound of claim 1 which is 6-(3-methyl-4-chlorophenyl)-2-(2-hydroxybutyl)-4,5-dihydropyridazin(2H)-3-one.

10. The compound of claim 1 which is 6-(p-chlorophenyl)-2-(2-hydroxybutyl)-5-methyl-4,5-dihydropyridazin(2H)-3-one.

11. The compound of claim 1 which is 6-(p-chlorophenyl)-2-(2-hydroxybutyl)-4,4-dimethyl-4,5-dihydropyridazin(2H)-3-one.

12. The compound of claim 1 which is 6-(p-chlorophenyl)-2-(2-hydroxybutyl)-4-methyl-,4,5-dihydropyridazin(2H)-3-one.

* * * * *